United States Patent
Constantz et al.

(10) Patent No.: US 6,719,747 B2
(45) Date of Patent: *Apr. 13, 2004

(54) PROTON GENERATING CATHETERS AND METHODS FOR THEIR USE IN ENHANCING FLUID FLOW THROUGH A VASCULAR SITE OCCUPIED BY A CALCIFIED VASCULAR OCCULATION

(75) Inventors: Brent R. Constantz, Cupertino, CA (US); John Ross, La Jolla, CA (US)

(73) Assignee: Corazon Technologies, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/358,983

(22) Filed: Feb. 4, 2003

(65) Prior Publication Data

US 2003/0171709 A1 Sep. 11, 2003

Related U.S. Application Data

(63) Continuation of application No. 09/753,023, filed on Dec. 29, 2000, now Pat. No. 6,540,733.

(51) Int. Cl.[7] ............................................... A61M 31/00
(52) U.S. Cl. ..................................... 604/507; 128/898
(58) Field of Search ............................ 604/20, 21, 22, 604/501, 93.01, 96.01, 104, 264, 523, 532, 607; 606/191, 192, 194

(56) References Cited

U.S. PATENT DOCUMENTS

| 4,445,892 A | 5/1984 | Hussein et al. |
|---|---|---|
| 4,573,966 A | 3/1986 | Weikl et al. |
| 4,610,662 A | 9/1986 | Weikl et al. |
| 4,636,195 A | 1/1987 | Wolinsky |
| 4,655,746 A | 4/1987 | Daniels et al. |
| 4,690,672 A | 9/1987 | Veltrup |
| 4,824,436 A | 4/1989 | Wolinsky |
| 4,842,598 A | 6/1989 | Tran |
| 4,911,163 A | 3/1990 | Fina |
| 4,976,733 A | 12/1990 | Girardot |
| 5,059,178 A | 10/1991 | Ya |
| 5,090,960 A | 2/1992 | Don Michael |
| 5,167,628 A | 12/1992 | Boyles |
| 5,195,955 A | 3/1993 | Don Michael |
| 5,222,941 A | 6/1993 | Don Michael |
| 5,222,971 A | 6/1993 | Willard et al. |
| 5,354,295 A | 10/1994 | Guglielmi et al. |
| 5,370,609 A | 12/1994 | Drasler et al. |
| 5,380,284 A | 1/1995 | Don Michael |
| 5,441,498 A | * 8/1995 | Perkins .................. 606/15 |
| 5,443,446 A | 8/1995 | Shturman |
| 5,454,809 A | * 10/1995 | Janssen .................. 606/41 |
| 5,462,529 A | 10/1995 | Simpson et al. |
| 5,496,267 A | 3/1996 | Drasler et al. |
| 5,718,701 A | 2/1998 | Shai et al. |
| 5,730,704 A | 3/1998 | Avitall |
| 5,772,590 A | 6/1998 | Webster, Jr. |
| 5,779,699 A | 7/1998 | Lipson |

(List continued on next page.)

Primary Examiner—Edward K. Look
Assistant Examiner—John F. Fristoe, Jr.
(74) Attorney, Agent, or Firm—Bret Field; Bozicevic, Field & Francis LLP

(57) ABSTRACT

Catheter devices and methods are provided for enhancing fluid flow through a vascular site occupied by a calcified lesion. The catheter devices of the subject invention at least include, at their distal end, a proton generating means, and in many embodiments also include a flushing means. In using the subject devices, the distal end of the catheter is placed proximal to the vascular occlusion and protons are generated, e.g., via proton generation from water, in a manner sufficient to reduce the pH of the vascular site in the region proximal to the occlusion. The subphysiologic pH is maintained for a period of time sufficient for fluid flow through the vascular site to be enhanced. Also provided are kits comprising the subject catheter devices for use in the subject methods.

19 Claims, 2 Drawing Sheets

U.S. PATENT DOCUMENTS

| | | |
|---|---|---|
| 5,782,239 A | 7/1998 | Webster, Jr. |
| 5,782,898 A | 7/1998 | Dahl et al. |
| 5,785,675 A | 7/1998 | Drasler et al. |
| 5,792,140 A | 8/1998 | Tu et al. |
| 5,814,076 A | 9/1998 | Brownlee |
| RE35,924 E | 10/1998 | Winkler |
| 5,817,093 A | 10/1998 | Williamson, IV et al. |
| 5,827,272 A | 10/1998 | Breining et al. |
| 5,827,278 A | 10/1998 | Webster, Jr. |
| 5,833,650 A | 11/1998 | Imran |
| 5,836,875 A | 11/1998 | Webster, Jr. |
| 5,836,990 A | 11/1998 | Li |
| 5,837,001 A | 11/1998 | Mackey |
| 5,843,152 A | 12/1998 | Tu et al. |
| 5,848,972 A | 12/1998 | Triedman et al. |
| 5,853,425 A | 12/1998 | Houser |
| 5,860,974 A | 1/1999 | Abele |
| 5,871,444 A | 2/1999 | Ouchi |
| 5,879,295 A | 3/1999 | Li et al. |
| 5,885,277 A * | 3/1999 | Korth .................... 606/35 |
| 5,891,135 A | 4/1999 | Jackson et al. |
| 5,893,884 A | 4/1999 | Tu |
| 5,893,885 A | 4/1999 | Webster, Jr. |
| 5,897,554 A | 4/1999 | Chia et al. |
| 5,902,610 A * | 5/1999 | Hausheer et al. ............ 424/649 |
| 5,916,158 A | 6/1999 | Webster, Jr. |
| 5,916,163 A | 6/1999 | Panescu et al. |
| 5,931,835 A | 8/1999 | Mackey |
| 5,935,063 A | 8/1999 | Nguyen |
| 5,935,102 A | 8/1999 | Bowden et al. |
| 5,935,124 A | 8/1999 | Klumb et al. |
| 5,938,659 A | 8/1999 | Tu et al. |
| 5,938,694 A | 8/1999 | Jaraczewski et al. |
| 5,941,845 A | 8/1999 | Tu et al. |
| 5,997,532 A | 12/1999 | McLaughlin et al. |
| 5,997,536 A | 12/1999 | Osswald et al. |
| 6,156,350 A * | 12/2000 | Constantz ............... 424/666 |
| 6,379,345 B1 * | 4/2002 | Constantz ............... 128/898 |
| 6,387,071 B1 * | 5/2002 | Constantz ............... 128/898 |
| 6,394,096 B1 * | 5/2002 | Constantz ............... 128/898 |

* cited by examiner

PROTON GENERATING CATHETERS AND METHODS FOR THEIR USE IN ENHANCING FLUID FLOW THROUGH A VASCULAR SITE OCCUPIED BY A CALCIFIED VASCULAR OCCULATION

INTRODUCTION

1. Technical Field

The field of this invention is vascular disease, particularly vascular diseases characterized by the presence of calcified vascular occlusions.

2. Background of the Invention

Vascular occlusions, which may be partial or total occlusions, play a prominent role in many types of vascular disease. Many vascular occlusions encountered in the treatment of vascular disease are characterized by having a mineral component, i.e., they are calcified. Calcified vascular occlusions, both partial and total, are found in both peripheral and coronary vascular disease.

A variety of different protocols have been developed for treating vascular diseases characterized by the presence of partial or total occlusions. Such treatment methodologies generally involve mechanical removal or reduction of the size of the occlusion, and include: bypass surgery, balloon angioplasty, mechanical debridement, atherectomy, and the like.

Despite the plethora of different treatment strategies that have been developed for the treatment of vascular diseases associated with vascular occlusions, there are disadvantages associated with each technique, such as tissue damage, invasiveness, etc. For example, restenosis is a common complication that results in arteries in which occlusions have been mechanically removed.

Calcified vascular occlusions pose significant challenges to currently employed treatment methodologies. For example, where the target vascular occlusion is a total occlusion, it is difficult if not impossible to pass a guidewire through the occlusion, which step is required for many of the currently used procedures. While bypass grafts are sometimes available as alternatives in such instances, bypass procedures have their own risks and complications. As such, there is continued interest in the development of endovascular methods of treating vascular occlusions. Of particular interest would be the development of methods and devices suitable for use in the treatment of calcified vascular occlusions.

Relevant Literature

U.S. Patents of interest include: U.S. Pat. Nos. 4,445,892; 4,573,966; 4,610,662; 4,636,195; 4,655,746; 4,690,672; 4,824,436; 4,911,163; 4,976,733; 5,059,178; 5,090,960; 5,167,628; 5,195,955; 5,222,941; 5,370,609; 5,380,284; 5,443,446; 5,462,529; 5,496,267; 5,785,675; and 5,833,650.

Catheter devices having electrodes positioned at their distal ends include those described in U.S. Pat. Nos. 5,997,536; 5,997,532; 5,941,845; 5,938,694; 5,938,659; 5,935,124; 5,935,102; 5,935,063; 5,931,835; 5,916,163; 5,916,158; 5,897,554; 5,893,885; 5,893,884; 5,891,135; 5,879,295; 5,871,444; 5,860,974; 5,853,425; 5,848,972; 5,843,152; 5,837,001; 5,836,990; 5,836,875; 5,827,278; 5,827,272; 5,817,093; 5,814,076; 5,792,140; 5,782,898; 5,782,239; 5,779,699; 5,772,590; 5,730,704; 5,718,701; and U.S. RE Pat. No. 35,924.

SUMMARY OF THE INVENTION

Catheter devices and methods are provided for enhancing fluid flow through a vascular site occupied by a calcified lesion. The catheter devices of the subject invention at least include, at their distal end, a proton generating means, and in many embodiments also include a flushing means. In using the subject devices, the distal end of the catheter is placed proximal to the vascular occlusion and protons are generated, e.g., via proton generation from water, in a manner sufficient to reduce the pH of the vascular site in the region proximal to the occlusion. The sub-physiologic pH is maintained for a period of time sufficient for fluid flow through the vascular site to be enhanced. Also provided are kits that include the subject catheter devices for use in the subject methods.

DESCRIPTION OF THE SPECIFIC EMBODIMENTS

Figure 1:
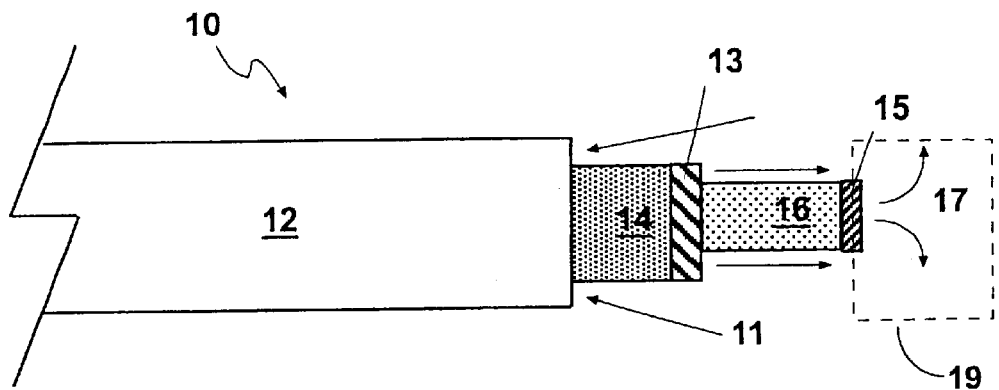
FIG. 1 provides a representation of a first catheter device according to the subject invention.

Catheter devices and methods are provided for enhancing fluid flow through a vascular site occupied by a calcified lesion. The catheter devices of the subject invention at least include, at their distal end, a proton generating means, and in many embodiments also include a flushing means. In using the subject devices, the distal end of the catheter is placed proximal to the vascular occlusion and protons are generated, e.g., via proton generation from water, in a manner sufficient to reduce the pH of the vascular site in the region proximal to the occlusion. The sub-physiologic pH is maintained for a period of time sufficient for fluid flow through the vascular site to be enhanced. Also provided are kits that include the subject catheter devices for use in the subject methods.

In further disclosing the subject invention, the subject devices will be described first in greater detail, followed by a more in depth discussion of the subject methods, systems and kits.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Catheter Devices

As summarized above, the subject invention provides catheter devices that include, at their distal end, at least a proton generating means, wherein many embodiments, the devices also include a vascular site flushing means. By catheter device is meant an elongated structure which is capable of being introduced into and moved through the vascular system of a host. Typically, the subject catheter devices are elongated tubular structures that can be introduced into the vascular site at a location remote to a target vascular site and moved through the vascular system to the target site. Since they are designed to be introduced into the vascular system of a host, the subject catheter devices have cross-sectional outer diameters ranging from about 1 mm to 5 mm, usually from about 2 mm to 3 mm, where the diameter may be constant or varied along the length of the device. The subject catheter devices are also characterized by having a distal end and a proximal end, where the distal end is the end which is next to or at the vascular site during use, i.e., the end that is present inside the vascular system of the host, and the proximal end is that end which is outside of the host during use, i.e., the end that is connected to a manifold, etc., during use.

A feature of the subject catheter devices is that they include a proton generating means at their distal end. The proton generating means is, in the broadest sense, any means that is capable of generating protons from water in the vascular site. In many embodiments, the proton generating means is an electrode means for generating protons from water present in the vascular site. In other words, the proton generating means includes an anode and a cathode which, upon application of a current, generate protons from water in the vascular site, and thereby provide for a subphysiological pH in at least a region of the vascular site.

The electrodes that make up the anode and the cathode of the proton generation means may be arranged at the distal end in any convenient configuration, so long as the configuration is capable of providing for the requisite proton generation upon current application to the electrodes. As such, one electrode may be a wire that passes through a ring counterelectrode, two spaced apart ring electrodes may be present, etc. The distance between the cathode and the anode is sufficient to provide for the requisite proton formation, where the distance between the two electrodes typically ranges in many embodiments from about 0.1 mm to 10 mm, usually from about 0.25 mm to 5 mm and more usually from about 0.5 mm to 2 mm. In many embodiments, the anode is positioned more distal than the cathode, such that the anode is closer than the cathode to the vascular occlusion during use. Representative configurations are described in greater detail supra in terms of the figures.

As mentioned above, also present at the distal end of the subject catheters in many embodiments is a means for flushing the vascular space with an aqueous fluid, e.g., water, water that has one or more solutes, e.g., Na$^+$, K$^+$, Cl$^-$, etc., such as an electrolyte solution, and the like. The flushing means typically includes an opening of a first lumen through which fluid leaves the catheter device and enters the vascular site and a second opening through which fluid leaves the vascular site and enters the catheter device, e.g., such as is found in the multilumen catheters described in PCT patent application published under the publication number WO 00/03651 and the priority applications cited therein, the disclosures of which priority applications are herein incorporated by reference.

In certain embodiments, the catheter devices may include a vascular occlusion means. In these embodiments, the subject catheter devices are further characterized by at least including a first vascular occlusion means positioned at some point proximal to the distal end of the outer surface of the catheter device, e.g., the outer surface of the aspiration catheter in the coaxial embodiments described infra. By vascular occlusion means is meant any device or component that is capable of substantially, and preferably completely, occluding a vessel, e.g., an artery or vein. By substantially occluding is meant that fluid, e.g. blood, flow past the occlusion means upon activation is reduced by at least 95%, usually by at least 97% and more usually by at least 99%, where in preferred embodiments, fluid flow is reduced by 100% such that the fluid flow into the vascular site is substantially, if not completely, inhibited. Any convenient means may be employed, where a vascular occlusion means of particular interest includes an inflatable balloon. Inflatable balloons are well known in the catheter art, and any convenient balloon configuration may be employed. While the inflatable balloon may be one that is designed to be inflated with a gas or liquid, of particular interest in many embodiments are those that are configured to be inflated with a liquid, e.g. a pH elevating or buffer solution as described in greater detail infra.

The catheter devices may be single integral devices or composites of two or more disparate elements. Thus, the catheter devices may comprise all of the elements that make up the device, e.g., the electrodes, the lumens, etc., as a single structure, i.e., on a structure where no two of these elements are capable of moving relative independently of each other. Alternatively, the devices may be made up of two or more distinct elements that can be moved independently of each other, e.g., coaxial lumens, etc., where representative embodiments are described infra in greater detail.

Turning now to the figures, FIG. 1 provides a depiction of the distal tip of a catheter device according to a first embodiment of the subject invention. Distal end 10 of the catheter device has two electrodes, the anode 15 and the cathode 13. Anode 15 and cathode 13 are ring electrodes at the end of tubular elements 16 and 14, respectively, which tubular elements are, in turn, slidably positioned inside of outer tubular element 12. As such, tubular elements 12, 14 and 16 are coaxial and make up the catheter device. During use, fluid is introduced into the vascular space through the opening at the distal end of element 16 in the direction 17 and is removed from the vascular space via the annular opening 11 in the direction of the arrows. The zone 19 indicates the area of reduced pH that is produced during use.

Figure 2:
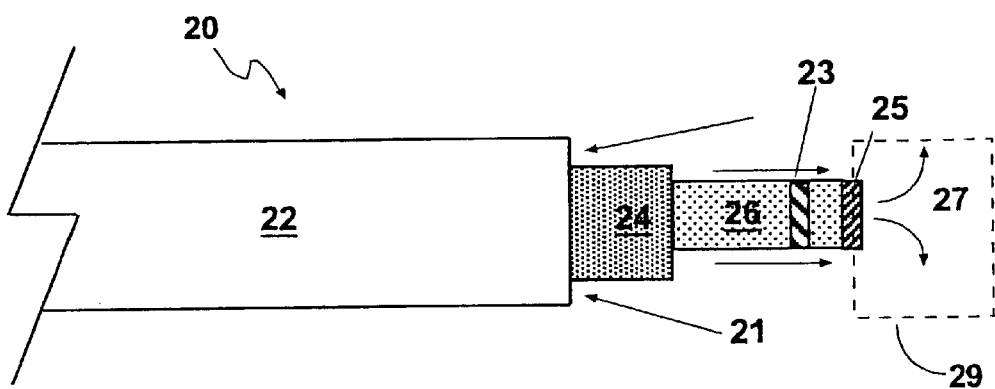
FIG. 2 provides a representation of a second catheter device according to the subject invention.

FIG. 2 provides a depiction of the distal tip of a catheter device according to a second embodiment of the subject invention. Distal end 20 of the catheter device has two electrodes, the anode 25 and the cathode 23. Anode 25 and cathode 23 are ring electrodes positioned at the end of the same tubular element 26, which tubular element is, in turn, slidably positioned inside of outer tubular elements 24 and 22. As such, tubular elements 22, 24 and 26 are coaxial and make up the catheter device. During use, fluid is introduced into the vascular space through the opening at the distal end of element 26 in the direction 27 and is removed from the vascular space via the annular opening 21 in the direction of the arrows. The zone 29 indicates the area of reduced pH that is produced during use.

Figure 3:
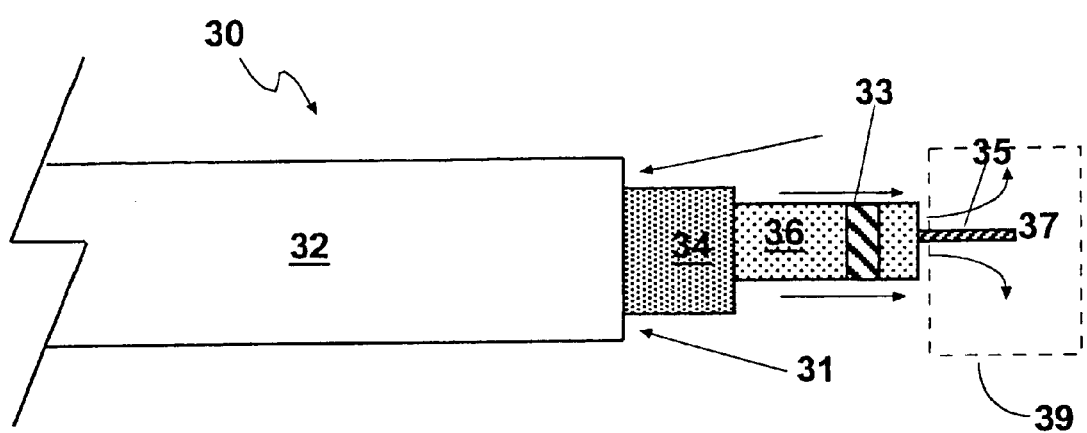
FIG. 3 provides a representation of a third catheter device according to the subject invention.

FIG. 3 provides a depiction of the distal tip of a catheter device according to a third embodiment of the subject invention. Distal end 30 of the catheter device has two electrodes, the anode 35 and the cathode 33. In this embodiment, the anode 35 is a wire electrode and cathode 33 is a ring electrode positioned at the end of the tubular element 36, which tubular element is, in turn, slidably positioned inside of outer tubular elements 34 and 32. As such, tubular elements 32, 34 and 36 are coaxial and make up the catheter device. During use, fluid is introduced into the vascular space through the opening at the distal end of element 36 in the direction 37 and is removed from the vascular space via the annular opening 31 in the direction of the arrows. The zone 39 indicates the area of reduced pH that is produced during use.

The above described specific embodiments are merely representative embodiments of the subject catheter devices. Other configurations are possible and are intended to come within the scope of the present invention.

Methods

As summarized above, also provided by the subject invention are methods for enhancing fluid flow through a vascular site occupied by a vascular occlusion, e.g., a partial or total occlusion. For treatment of vascular calcified occlusions with the subject catheter devices, the subject catheter devices are used to generate protons in at least a region of the vascular site proximal to the lesion in a manner sufficient to provide for a subphysiological pH in the region which ultimately results in enhancement of fluid flow through the target vascular site. By enhanced is meant that fluid flow is either established in situations where fluid flow is not initially present, e.g., where the target vascular occlusion is a total occlusion, or increased where some fluid flow through the vascular site is present, e.g., in situations where the vascular site is occupied by a partial occlusion.

The Target Vascular Site

The target site through which fluid flow is enhanced by the subject methods is a site within a vessel, typically an artery or vein, and usually an artery. In many embodiments, the vascular site is a peripheral vascular site, by which is meant that the vessel in which the vascular site is located is a vessel found in one of the extremities of the patient to be treated, i.e., the arms or legs. Often, the vascular site is a site in a lower extremity vessel, e.g., a lower extremity artery. As indicated above, of particular interest in certain embodiments are peripheral arterial vascular sites, where specific peripheral arteries of interest include: iliac arteries, femoropopliteal arteries, infrapopliteal arteries, femoral arteries, superficial femoral arteries, popliteal arteries, and the like. In yet other embodiments, the vascular site is present in a heart associated vessel, e.g., the aorta, a coronary artery or branch vessel thereof, etc. In yet other embodiments, the vascular site is present in a carotid artery or a branch vessel thereof.

The vascular site is occupied by a vascular occlusion in such a manner that fluid flow through the vascular site, e.g., blood flow, is at least impeded if not substantially inhibited. By at least impeded is meant that fluid flow is reduced by at least 20%, usually by at least 50% and more usually by at least 80% through the vascular site as compared to a control. In such situations, the vascular site is occupied by a partial vascular calcified occlusion. By substantially inhibited is meant that substantially no fluid flows through the vascular site. For purposes of this invention, fluid flow through a vascular site is considered to be substantially inhibited where it is not possible to pass a guidewire through the vascular site, where the guidewire has a diameter ranging from 0.014 to 0.038 in and is applied to the site with a pressure ranging from about 1 to 30 oz.

The Target Vascular Occlusion

The vascular occlusion that occupies the target vascular site is generally a calcified vascular occlusion, by which is meant that the occlusion includes at least some calcium containing component. The calcified occlusion may be a substantially pure mineral structure, or may be a more complex formation that includes both mineral and other components, including organic matter, e.g., lipids, proteins, and the like. As mentioned above, the target vascular occlusion may be a partial or total vascular occlusion.

The mineral component making up the calcified lesion is generally made up of one or more calcium phosphates, where the calcium phosphates are generally apatitic. The mineral component of the calcified occlusion typically includes one or more of hydroxyapatite, carbonated hydroxyapatite (dahllite) and calcium deficient hydroxyapatite.

In addition to the mineral component, the calcified occlusion that occupies the target vascular site may also comprise one or more additional components, where such components include: lipids; lipoproteins; proteins; including fibrinogen, collagen, elastin and the like; proteoglycans, such as chondroitin sulfate, heparin sulfate, dermatans, etc.; and cells, including smooth muscle cells, epithelial cells, macrophages and lymphocytes. As such, calcified occlusions that are targets of the subject methods include those that may be described as: type IV, type V and type VI lesions, as defined in Stary et al., Arterioscler. Thromb. Vasc. Biol. (1995) 15:1512–1531.

In the vascular occlusions that occupy the target vascular sites of many embodiments of the subject methods, the mineral component of the calcified occlusion generally makes up from about 10 to 100, usually from about 10 to 90 and more usually from about 10 to 85 dry weight % of the occlusion. The size of the occlusion that is the target of the subject methods varies depending on location and specific nature of the occlusion. Generally, the volume of the occlusion ranges from about 20 to 10,000 $mm^3$, usually from about 30 to 500 $mm^3$ and more usually from about 50 to 300 $mm^3$.

In certain embodiments, one or both ends of the occlusion may be characterized by being primarily thrombotic material, e.g., a thrombus, where the thrombotic domain of the occlusion extends for about 1 to 5 cm. The nature of the thrombotic domain may be organized or disorganized.

Fluid Flow Enhancement

In the subject methods, fluid flow is enhanced through the vascular site by generating protons in the vascular site in a manner sufficient to provide for a region of subphysiological pH at least proximal to the calcified vascular occlusion. Protons may be generated using any convenient protocol, where one protocol of interest is to generate the protons from water present in the vascular site by electrode means, i.e., with an anode and a cathode. In the subject methods, protons are generated in the region of the vascular site next to or adjacent to the lesion such that the pH of this region is generally less than about 6, usually less than about 4 and in many embodiments less than about 2, where in certain embodiments the pH in this region during practice of the subject methods does not exceed about 1.

When an anode and a cathode are employed to generate the protons and thereby provide for the region of subphysiologic pH, an electric potential is applied between the two electrodes, where the magnitude of the electric potential is sufficient to provide for the requisite proton generation from water. The magnitude of the electric potential that is applied between the two electrodes, i.e., the anode and the cathode, typically ranges from about 1 V to 10 V, usually from about 1 V to 3 V and more usually from about 1.3 V to 2 V. Any convenient means for applying the electric potential between the two electrodes may be employed, where means of interest include direct current (DC) means and alternating current (AC) means, as well as pulsed current means. The particular means chosen will depend primarily on the particular protocol employed and the specific nature of proton generation desired.

While in certain embodiments the requisite protons are generated from water present in the vascular site, e.g., plasma present in the vascular site, in many preferred embodiments of the subject invention, the vascular site is flushed with an aqueous fluid concomitant with proton generation so as to provide for a constant source of water to be used in proton generation and to remove fluid and debris, including dissolved and/or particulate calcium phosphate mineral, from the vascular site.

Is these embodiments that include flushing the vascular site with an aqueous fluid, it is preferred that the pressure in the local environment which includes the surface of the occlusion, i.e., the area bounded by the vessel walls, the surface of the target occlusion and the catheter system used to deliver the solution, remains substantially isobaric. By substantially isobaric is meant that the pressure in the local environment does not vary by a significant amount, where the amount of variance over the treatment period does not vary by more than about 50%, usually by not more than about 10% and more usually by not more than about 5%. In other words, the local environment remains substantially isobaric during the treatment period. Accordingly, where fluid is dynamically contacted with the surface of the target occlusion, fluid is also simultaneously removed from the local environment comprising the surface of the target occlusion, such that the overall volume of fluid in the local environment remains substantially constant, where any difference in volume at any two given times during the treatment period does not exceed about 50%, and usually does not exceed about 10%. As such, the aqueous fluid is introduced into the local environment of the target lesion in a manner such that the local environment remains substantially isovolumetric.

A variety of different types of aqueous fluids may be employed in the subject methods. The term aqueous fluid is used broadly to refer to not only pure water, e.g., water for injection or WFI, but also water that includes one or more distinct solutes, e.g., electrolytes. As such, the term aqueous fluid also includes electrolyte solutions. Electrolyte or salt solutions of interest include NaCl solutions, e.g., phosphate buffered saline, and other physiologically acceptable analogous salt solutions, as are known in the art, and the like.

When employed, the aqueous fluid is introduced in a manner such that the flow rate of the fluid through the vascular site of the lesion is generally at least about 10 cc/min, usually at least about 20 cc/min and more usually at least about 60 cc/min, where the flow rate may be as great as 120 cc/min or greater, but usually does not exceed about 1000 cc/minute and more usually does not exceed about 500 cc/minute, where by "volume" is meant the local environment of the occlusion, as defined above. The total amount of fluid that is passed through the local environment of the lesion during the treatment period typically ranges from about 100 to 1000 cc, usually from about 200 to 800 cc and more usually from about 400 to 500 cc. The solution is generally pressurized to achieve the desired flow rate, as described supra. As such, the pressure at the proximal end of the coaxial catheter assembly through which the solution enters the catheter and is thereby introduced into the local environment typically ranges from about 50 to 1200 psi, usually from about 100 to 600 psi and more usually from about 200 to 400 psi. It is important to note that in many embodiments of the subject invention the overall pressure in the local environment is maintained at substantially isometric or isobaric conditions. As such, the negative pressure at the entrance to the aspiration catheter, e.g., the open annulus at the distal end of the aspiration catheter will be of sufficient magnitude to provide for substantially isobaric conditions. Preferably, the overall pressure in the local environment is maintained at a value ranging from about 0.1 to 3 psi, usually from a bout 0.5 to 2.5 psi and more usually from about 1 to 2 psi. This lower, isobaric pressure is maintained through proper control of the flow rate into and out of the local site, e.g., through proper control of fluid introduction and aspiration.

Time Period

In the subject methods, the subphysiologic pH is maintained in the vascular site, e.g., through proton generation in the vascular site, for a period of time sufficient for fluid flow to be enhanced or established through the vascular site, e.g., established or improved. As such, where the target occlusion is a total occlusion, subphysiologic pH is maintained for a period of time sufficient for a guidewire to be passed through the vascular site, as described above. Alternatively, where the target occlusion is a partial occlusion, subphysiologic pH is maintained for a period of time sufficient for the rate of fluid flow to be increased through the vascular site, generally by at least about 10%, usually by at least about 50%, and in many embodiments by at least about 100%. Generally, the period of time during which subphysiologic pH is maintained proximal to the target occlusion ranges from about 5 to 100 minutes, usually from about 10 to 30 minutes.

Further Embodiments of the Subject Methods

In a number of embodiments of the subject methods, the above described basic methods may be modified to include a number of additional method steps. Additional method steps that may be present in the overall process include: rendering the local environment of the target occlusion bloodless, washing or rinsing the local environment of the target occlusion, applying external energy to the target occlusion; imaging the target vascular site; establishing or expanding a passageway through an initial thrombotic domain of the target occlusion; and the like.

Rendering the Local Environment Bloodless

In certain embodiments, as described above, the local environment of the target occlusion is rendered substantially bloodless prior to introduction of the aqueous fluid. In these embodiments, the balloon(s) of the assembled catheter system is inflated to physically isolate the local environment from the remainder of the circulatory system and then the local environment is flushed with a physiologically acceptable solution, such that substantially all of the blood present in the solution is removed. Typically, a washing solution will be employed in this step of rendering the local environment bloodless. Examples of washing solutions that may find use in these embodiments include: water for injection, saline solutions, e.g., Ringer's, phosphate buffered saline, or other physiologically acceptable solutions. The washing solution includes an anticlotting factor in many embodiments, where anticlotting factors of interest include heparin and the like. The washing solution can also contain chelating agents.

Application of External Energy

In certain embodiments, external energy is applied to the vascular site to promote mechanical break-up of the occlusion into particles or debris that can be easily removed from the vascular site. Any means of applying external energy to the vascular site may be employed. As such, jets or other such means on a catheter device which are capable of providing varying external forces to the occlusion sufficient to cause the occlusion to break up or disrupt the occlusion may be employed. Of particular interest in many embodiments is the use of ultrasound. The ultrasound can be applied during the entire time of contact of the cardiovascular tissue with the acidic treatment solution, or the ultrasound can be applied for only part of the treatment period. In one embodiment, ultrasound is applied for several short periods of time while the dissolution treatment solution is contacted with the target occlusion. There are several devices for the application of ultrasound to cardiovascular tissue known to those of skill in the art. See e.g. U.S. Pat. No. 4,808,153 and U.S. Pat. No. 5,432,663, the disclosures of which are herein incorporated by reference.

In such methods where external energy is applied to the occlusion in order to disrupt or break-up the occlusion into particles or debris, the particles or debris may range in size from about 0.01 to 4.0 mm, usually from about 0.1 to 2.0 mm and more usually from about 0.5 to 1.0 mm. In such instances, the method may further include a step in which the resultant particles are removed from the vascular site. Particles may be removed from the vascular site using any convenient means, such as the catheter of the subject invention described in greater detail infra.

Another means that may be employed to apply external energy to the lesion during the dissolution process is to use a mechanical means of applying external energy. Mechanical means of interest include moving structures, e.g., rotating wires, guidewires, which physically contact the target occlusion and thereby apply physical external energy to the target lesion.

Imaging

In addition, it may be convenient to monitor or visualize the vascular site prior to or during treatment. A variety of suitable monitoring means are known to those of skill in the art. Any convenient means of invasive or noninvasive detection and/or quantification may be employed. Such means include plain film roentgenography, coronary arteriography, fluoroscopy, including digital subtraction fluoroscopy, cinefluoroscopy, conventional, helical and electron beam computed tomography, intravascular ultrasound (IVUS), magnetic resonance imaging, transthoracic and transesophageal echocardiography, rapid CT scanning, antioscopy and the like. Any of these means can be used to monitor the vascular site before, during or after proton generation in the vascular site.

Thrombus Removal Step

The subject methods may further include a thrombus removal step, e.g., where the calcified domain of the target occlusion is covered by a thrombotic domain, as described above. In such methods, any thrombus removal means that is capable of providing sufficient access of the eelectrode assembly and protons generated thereby to the surface the calcified domain of the target lesion may be employed. Thus, where the thrombotic domain is a disorganized domain, it may be sufficient to pass increasingly larger diameter guidewires through the domain until a passageway of sufficient width to provide access of the catheter assembly described above to the surface of the occlusion is established. Alternatively, portions of the thrombotic domain may be removed, e.g., via atherectomy methods, angioplasty methods, and the like, where devices for performing such procedures are known to those of skill in the art. See the patent references cited in the Relevant Literature section, supra, which references are herein incorporated by reference.

In yet other embodiments, the thrombus may be removed with RF ablation using techniques known to those of skill in the art. The RF ablation may be effected by using the proton generating electrodes to provide RF cutting action, e.g., by alternating application of a proton generating current to the electrodes with application of RF to the electrodes, or by using a separate set of RF electrodes present in the catheter device. RF devices and methods for their use are described in U.S. Pat. Nos. 6,059,778; 6,050,994; 6,015,407; 5,865,788; 5,807,395; 5,785,705; 5,720,718; 5,545,161; 5,423,811; 5,348,554; 5,098,431; and 4,936,281; the disclosures of which are herein incorporated by reference.

Outcome

As discussed above, the subject methods result in the enhancement of fluid flow through the vascular site occupied by the occlusion. Fluid flow is considered to be enhanced in those situations where the vascular site is totally occluded when a guide wire can be moved through the vascular site without significant resistance. Fluid flow is considered to be enhanced in those situations in which the vascular site is partially occluded when the rate of fluid flow through the vascular site increases by at least 10%, usually by at least 50% and in many embodiments by at least 100%.

In certain embodiments, the subject methods will not result in complete removal of the target occlusion from the vascular site. As such, the vascular site, while not totally occluded, may still include lesion deposits on the wall which impede fluid flow through the vascular site and the removal or reduction of which is desired. Any convenient protocol for treating these remaining deposits may be employed, e.g., balloon angioplasty, atherectomy, stenting, etc.

Systems

Also provided by the subject invention are systems for practicing the subject methods, i.e., for enhancing fluid flow through a vascular site occupied by a vascular occlusion. The subject systems at least include the catheter systems as described above, a manifold, a fluid reservoir for storing aqueous fluid and a negative pressure means for providing aspiration or suction during use of the system. The systems may further include a number of optional components, e.g., guidewires, pumps for pressurizing fluids, and the like. See e.g., U.S. patent application Ser. No. 09/384,860, the disclosure of which is herein incorporated by reference.

Utility

The subject devices and methods find use in a variety of different applications in which it is desired to enhance fluid flow, usually blood flow, (or at least pass a guidewire through), a vascular site that is occupied by a calcified vascular occlusion, e.g., a partial or total occlusion. As such, the subject methods and devices find use in the treatment of peripheral vascular disease, etc. The subject methods also find use in the treatment of coronary vascular diseases. By treatment is meant that a guidewire can at least be passed through the vascular site under conditions which, prior to treatment, it could not. Treatment also includes situations where the subject methods provide for larger fluid passageways through the vascular site, including those situations where fluid flow is returned to substantially the normal rate through the vascular site. The subject methods may be used in conjunction with other methods, including balloon angioplasty, atherectomy, and the like, as part of a total treatment protocol.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

Additional Utility

The subject devices also find use in methods of preventing restinosis, as described in U.S. Pat. No. 6,156,350, the disclosure of which is herein incorporated by reference. In the methods U.S. Pat. No. 6,156,350, a vascular site of a host is contacted with a solution having a sub-physiologic pH, e.g. a solution having a pH of less than about 4. The vascular site is contacted with the solution of reduced pH for a period of time sufficient for at least the progression of restinosis at the vascular site to at least be slowed, if not prevented. The catheter devices of the present invention can be employed to create the solution of sub-physiologic pH at the vascular site and therefore prevent restinosis according to the methods of U.S. Pat. No. 6,156,350.

Kits

Also provided by the subject invention are kits for use in enhancing fluid flow through a vascular site occupied by an occlusion. The subject kits at least include a catheter device or system, as described above. The kits may further include one or more additional components and accessories for use with the subject catheter systems, including tubing for connecting the various catheter components with fluid reservoirs, syringes, pumping means, etc., connectors, one or more guidewires, dilators, vacuum regulators, etc. Other elements that may be present in the subject kits include various components of the systems, including manifolds, balloon inflation means, e.g., syringes, pumping means, negative pressure means etc.

Finally, the kits include instructions for practicing the subject methods, where such instructions may be present on one or more of the kit components, the kit packaging and/or a kit package insert.

The following examples are offered by way of illustration and not by way of limitation.

Experimental

I. A 50 year old male having a total occlusion in the superficial femoral is treated as follows.

1. The patient is heparinized using standard procedures.
2. An introducer sheath is placed either in the same leg to provide retrograde access or in the opposite leg to provide cross-over access.
3. A guidewire is inserted and advanced to the site of the total occlusion.
4. The catheter device depicted in FIG. 1 is inserted so that the distal end of the device is at the vascular site occupied by the total occlusion.
5. Contrast medium is then injected into the vascular site to confirm the location of the distal end of the catheter.
6. A sufficient amount of heparinized phosphate buffered saline is then injected through port into the vascular site or local environment and aspirated therefrom such that the local environment is rendered substantially bloodless.
7. An constant electric potential provided by an electrically connected DC source is then applied between the anode and cathode such that protons are generated in the vascular site and the pH of the vascular site at least proximal to the occlusion is decreased to 1. Concomitantly, a sodium chloride electrolyte solution is flushed through the vascular site.
8. As the occlusion is demineralized, the catheter insert is advanced independent of the aspiration catheter.
9. Once a passage through the occlusion sufficient to pass a guidewire through the occlusion is produced, the device is removed.

The above procedure results in fluid flow through the vascular site occupied by the lesion being reestablished, as evidenced by passing a guidewire through the vascular site.

It is evident from the above discussion and results that improved methods of enhancing blood flow through a vascular occlusion are provided. Specifically, the subject invention provides a means for readily establishing fluid flow through a vascular site totally occluded by a calcified vascular occlusion, which has heretofore been difficult to practice. As such, the subject invention provides a means for using less traumatic procedures for treating peripheral vascular disease, thereby delaying or removing the need for graft procedures and/or amputation. A critical feature of the subject devices and methods is that a simple catheter based device is employed, thereby providing for economical manufacture of the device and ease of use. As such, the subject invention represents a significant contribution to the field.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A catheter device consisting essentially of at its distal end:
    a proton generating means;
    a vascular site flushing means comprising separate fluid introduction and aspiration elements; and said catheter device generating protons in a manner sufficient to provide for a subphysiological pH in the vascular site.
2. The catheter device according to claim 1, wherein said proton generating means is an electrode means.
3. The catheter device according to claim 2, wherein said electrode means comprises:
    an anode; and
    a cathode.
4. The catheter device according to claim 3, wherein said catheter device further comprises a means for applying an electric potential between said cathode and said anode.
5. The catheter device according to claim 1, wherein said catheter device comprises at least two distinct elements which are movable relative to each other.
6. A catheter device consisting essentially of at its distal end:
    a proton generating means comprising an anode and a cathode;
    a fluid introduction means; and
    an aspiration means that is separate from said fluid introduction means.
7. The catheter device according to claim 6, wherein said catheter device comprises at least two distinct elements which are movable relative to each other.
8. The catheter device according to claim 6, wherein said catheter device further comprises a means for applying an electric potential between said cathode and said anode.
9. A method of enhancing fluid flow through a vascular site occupied by a vascular occlusion, said method comprising:
    (a) generating protons from water in said vascular site using a device according to claim 1 in a manner sufficient to provide for a subphysiological pH in said vascular site; and
    (b) maintaining said subphysiological pH in said vascular site for a period of time sufficient for fluid flow to be enhanced through said vascular site;
    whereby fluid flow is enhanced through said vascular site.
10. The method according to claim 9, wherein said method further comprises flushing said vascular site with an aqueous solution.
11. The method according to claim 10, wherein said aqueous solution is an electrolyte solution.
12. The method according to claim 10, wherein said protons are generated by electrolyzing water in said vascular site.
13. The method according to claim 9, wherein said vascular occlusion comprises calcium.
14. The method according to claim 9, wherein said occlusion is a total occlusion.

15. The method according to claim 9, wherein said occlusion is a partial occlusion.

16. A system for enhancing fluid flow through a vascular site occupied by a vascular occlusion, said system comprising:
   (a) a catheter device according to claim 1;
   (b) a manifold;
   (c) an aqueous fluid reservoir; and
   (d) a source of negative pressure.

17. The system according to claim 16, wherein said system further comprises a guidewire.

18. A kit for use in enhancing fluid flow through a vascular site occupied by a vascular occlusion, said kit comprising:
   a catheter device according to claim 1.

19. The kit according to claim 18, wherein said kit further comprises a guidewire.

* * * * *

UNITED STATES PATENT AND TRADEMARK OFFICE
CERTIFICATE OF CORRECTION

PATENT NO. : 6,719,747 B2
DATED : April 13, 2004
INVENTOR(S) : Constantz, Brent R. et al.

It is certified that error appears in the above-identified patent and that said Letters Patent is hereby corrected as shown below:

Title page,
Item [54], Title, should read -- PROTON GENERATING CATHETERS AND METHODS FOR THEIR USE IN ENHANCING FLUID FLOW THROUGH A VASCULAR SITE OCCUPIED BY A CALCIFIED VASCULAR OCCLUSION --.

Signed and Sealed this

Twenty-seventh Day of September, 2005

JON W. DUDAS
*Director of the United States Patent and Trademark Office*